United States Patent [19]

Okazaki et al.

[11] 4,371,472

[45] Feb. 1, 1983

[54] PROCESS FOR PREPARING CYSTEAMINE-S-SUBSTITUTED COMPOUNDS AND DERIVATIVES THEREOF

[75] Inventors: Tethuharu Okazaki, Sagamihara; Takeo Komukai, Atsugi; Saburo Uchikuga, Yokohama, all of Japan

[73] Assignee: Sogo Pharmaceutical Co. Ltd., Kanagawa, Japan

[21] Appl. No.: 231,113

[22] Filed: Feb. 3, 1981

[30] Foreign Application Priority Data

Feb. 4, 1980 [JP] Japan ................................. 55-011466

[51] Int. Cl.$^3$ ...................... C07F 9/02; C07C 161/05
[52] U.S. Cl. ............................ 260/453 RY; 260/944; 260/978
[58] Field of Search ................. 260/453 RY, 944, 978

[56] References Cited

U.S. PATENT DOCUMENTS 3,468,925 9/1969 Brois .......................... 260/453 RY

OTHER PUBLICATIONS

Calmon, et al., Ion Exchangers in Organic and Biochemistry, p. 659 Interscience Publishers, Inc., N.Y., 1957.
Kirk-Othmer, Encyclopedia of Chemical Technology, vol. 14, p. 102.
Dermer & Ham, Ethyleneimine and Other Aziridines, Academic Press, 1969, pp. 315-316.

Primary Examiner—Henry R. Jiles
Assistant Examiner—Robert C. Whittenbough
Attorney, Agent, or Firm—Browdy & Neimark

[57] ABSTRACT

A process for preparing a cysteamine-S-substituted compound involves reacting ethyleneimine or ethyleneimine derivatives with a thiosulfate or thiophosphate in the presence of a cation exchanger of a free type. Use of the cation exchanger of a free type in this reaction allows preparation of the cysteamine-S-substituted compound with an amazingly high purity in a high yield.

2 Claims, No Drawings

PROCESS FOR PREPARING CYSTEAMINE-S-SUBSTITUTED COMPOUNDS AND DERIVATIVES THEREOF

BACKGROUND OF THE INVENTION

1. Field of the Invention

This invention relates to a novel process for preparing cysteamine-S-substituted compounds and derivatives thereof. More particularly, the invention relates to a very useful and advantageous pollution-free process for preparing said compounds with high purity in a high yield, said process requiring only one step and involving no possibility of producing any harmful substance.

2. Description of the Prior Art

Cysteamine-S-substituted compounds and derivatives thereof are known as substances having a radiation protective activity. They are also very useful as intermediates for medicinal preparations.

For the preparation of said compounds, there has been generally employed a process according to which, as shown by the following formulae, an ethyleneimine derivative is ring-opened with hydrobromic acid to form a bromoalkylamine hydrobromide which then is reacted with a thiosulfate or thiophosphate.

(H. Bretschneider: Monatsh. Chem. 81, 372 (1950); S. Åkerfeldt: Acta Chem. Scand. 13, 1479 (1959)).

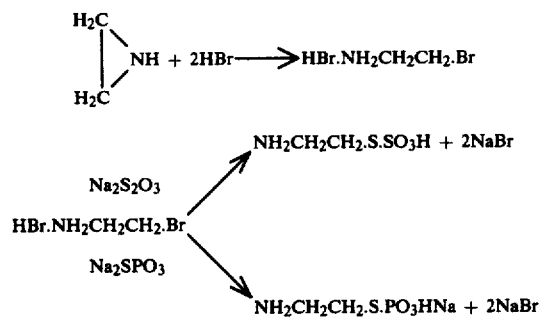

This known process, however, is very poor in yield: the overall yield from ethyleneimine is as low as 33.3% in the case of cysteamine-S-sulfuric acid (2-aminoethanethiosulfuric acid) and only 42.8% in the case of sodium monohydrogen cysteamine-S-phosphate. Further, as obvious from the above-shown reaction formulae, sodium bromide is formed as by-product at a rate of 2 moles to one mole of the objective material and, moreover, the objective material is readily soluble in water and shows the same behavior as the by-product sodium bromide, so that separation of the by-product sodium bromide is extremely difficult and its contamination in the final product is unavoidable. Thus, it is hardly possible with this process to obtain the objective substance with high purity.

Furthermore, according to the conventional process, the reaction can not be completed in one stage and needs to be carried out in two stages. In addition, it is essential in the first-stage reaction to use hydrobromic acid at a rate of 2 moles to one mole of ethyleneimine, said hydrobromic acid being a substance which, when exposed to air, produces bromine to give rise to the problem of environmental pollution and insanitation. To make the matter worse, the conventional process requires use of a large amount of this substance which is very expensive. Also, use of hydrobromic acid inevitably causes coloring of the products.

SUMMARY OF THE INVENTION

The present invention has been devised with the object of solving all of these problems. It is particularly noteworthy that the process of this invention has no need of using said trouble-making hydrobromic acid and, further, the reaction can be accomplished in one stage to produce the objective material alone, with no by-product formed. Besides, the process of this invention is capable of providing the objective material with higher purity in a higher yield than possible with the conventional process.

Thus, the present invention is based on the quite novel finding that when the following three substances: ethyleneimine, a cation exchanger of a free type, i.e. of H$^+$ form, and a thiosulfate or thiophosphate are properly associated with each other, there are derived the following advantages:

(a) ethyleneimine will not be polymerized with the cation exchanger of a free type which is a solid acid, (b) thiosulfate or thiophosphate will not be decomposed by the cation exchanger of a free type, (c) ethyleneimine is selectively reacted with the thiosulfate or thiophosphate, (d) cation exchange takes place selectively between the cation exchanger (free type) and the cations of the thiosulfate or thiophosphate, and (e) no exchange takes place between the cation exchanger of a free type and amino groups of the reaction product, that is, a cysteamine-S-substituted compound.

DETAILED DESCRIPTION OF THE INVENTION

This invention relates to a process for obtaining a high-purity cysteamine-S-substituted compound in a high yield by reacting ethyleneimine with a thiosulfate or thiophosphate in the presence of a cation exchanger of a free type, and the reaction according to this invention may be expressed by the following formula:

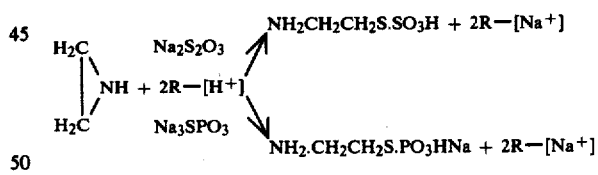

(wherein R-[H$^+$] represents a free-type cation exchanger).

As appreciated from the above-shown reaction system, participation of the three substances, that is, ethyleneimine, a cation exchanger of a free type and a thiosulfate or thiophosphate, is an essential requisite for the reaction of this invention.

A cation exchange resin is favorably used as the cation exchanger of a free type in this invention, and such cation exchange resin may be either strongly acidic or weakly acidic. As for the mode of use of said cation exchange resin, there may be employed either a static ion exchange method (a batch process) or a dynamic ion exchange method (a column process). Commercially available cation exchangers may be suitably used in an equivalent amount. A slight excess does not cause any noticeable drop of the yield.

As for the thiosulfate or thiophosphate, there may be properly used an alkali metal salt, an alkaline earth metal salt, an ammonium salt or the like, but use of a sodium salt is preferred for the reason of easy availability.

The solvent used in the reaction of this invention may be of any known type, such as water or alcohol, which does not take any part in the reaction, and such known solvents may be used either alone or in admixture.

The reaction temperature is preferably room temperature or below, for example near 0° C., and the reaction is completed in several hours.

According to the process of this invention, since the objective substance alone remains in the reaction solution and there scarcely exists any by-product, a high-purity cysteamine-S-substituted compound can be obtained in a high yield by merely separating the cation exchanger and the reaction solution, concentrating the solution and then crystallizing the product. The purity of cysteamine-S-substituted compounds and derivatives thereof affects directly the melting point (decomposition point), thereof, and the presence of even a trace amount of impurities results in a large drop of the melting point (decomposition point).

For showing the difference in product purity between the conventional process and the process of this invention, comparison of the melting points (decomposition points) of the products is shown in the following table by taking the case of cysteamine-S-sulfuric acid and a derivative thereof.

| Cysteamine-S-substituted compound | Conventional process | Process of this invention |
|---|---|---|
| Cysteamine-S-sulfuric acid | 184° C. | 190–193° C. |
| 2-Aminopropanethiolsulfuric acid | 193–195° C. | 200.5–201.5° C. |

As apparent from the above data, when ethyleneimine and a thiosulfate or thiophosphate are reacted in the presence of a cation exchanger of a free type, the reaction proceeds rapidly and selectively to give a high-purity cysteamine-S-substituted compound in a high yield.

The invention is further described below by way of the examples thereof.

EXAMPLE 1

8.6 g (0.20 mol) of ethyleneimine was dissolved in 50 ml of methanol, and the solution was added dropwise into a mixed solution of 49.6 g (0.20 mol) of sodium thiosulfate pentahydrate, 150 ml of water and 100 ml of methanol. To this mixed solution, with its pH maintained at above 5.5, was added a strongly acidic cation exchange resin (Diaion SK 1B[H+]) so that the solution would finally have a pH of 7 (220 ml of said resin was used). The reaction solution was refluxed with heating for one hour. After cooling, the solution was filtered and the filtrate was concentrated and evaporated to dryness. The crude yield was 30.6 g (97.9%). The obtained solid was recrystallized from water to give 29.8 g of white crystals of 2-aminoethanethiolsulfuric acid.

Yield: 94.8%; Melting point: 190°–192° C. (decomposed).

EXAMPLE 2

The same process as in Example 1 was carried out by using water alone as the reaction solvent.

Yield: 29.4 g, 93.5%; Melting point: 190°–191.5° C. (decomposed).

EXAMPLE 3

The same process as in Example 1 was carried out by using calcium thiosulfate as the thiosulfate.

Yield: 28.8 g, 91.6%; Melting point: 191.5°–192.5° C. (decomposed).

EXAMPLE 4

The same process as in Example 1 was carried out by using ammonium thiosulfate as the thiosulfate.

Yield: 29.0 g, 92.2%; Melting point: 191.5°–193° C. (decomposed).

EXAMPLE 5

The same process as in Example 4 was carried out by using a weakly acidic cation exchange resin (Diaion WK 10[H+]) as the ion exchanger.

Yield: 28.7 g, 91.3%; Melting point: 190°–191.5° C. (decomposed).

EXAMPLE 6

The same reaction as in Example 1 was performed by using 2-methylaziridine instead of ethyleneimide to obtain 2-aminopropanethiolsulfuric acid.

Yield: 30.0 g, 87.6%; Melting point: 200.5°–201.5° C. (decomposed); N: 8.08% (calculated: 8.18%).

EXAMPLE 7

The same reaction as in Example 1 was carried out by using 2,2-dimethylaziridine instead of ethyleneimine to obtain 2-amino-2-methylpropanethiolsulfuric acid.

Yield: 32.7 g, 88.2%;

Melting point: 242°–244° C. (decomposed); N: 7.53% (calculated: 7.56%).

EXAMPLE 8

8.6 g (0.20 mol) of ethyleneimine and 49.6 g (0.20 mol) of sodium thiosulfate pentahydrate were dissolved in 150 ml of water, and the solution was passed through 160 ml of a weakly acidic cation exchange resin (Diaion WK 10[H+]) (in a column with an inner diameter of 3 cm). The column was washed with 700 ml of desalted water, and the effluent and the rinse were joined and evaporated to dryness, and the obtained crystals were recrystallized from water to give 25.7 g of 2-aminoethanethiosulfuric acid.

Yield: 81.7%; Melting point: 190°–191.5° C. (decomposed).

EXAMPLE 9

8.6 g (0.2 mol) of ethyleneimine was dissolved in 50 ml of methanol, and the solution was added dropwise into a solution prepared by dissolving 36.0 g (0.2 mol) of sodium monothiophosphate in 300 ml of water.

Then 210 ml of a strongly acidic cation exchange resin (Diaion SK 1B[H+]) was gradually added into said mixture maintained at 0° C., and thereafter the mixture was stirred at room temperature for 3 hours, then at 60° C. for additional one hour, cooled and filtered.

The filtrate was decolored and concentrated to 100 ml at a bath temperature of below 60° C., and then 500 ml of ethanol was added thereto for crystallization. After filtration, the obtained crystals were dispersed in 1,000 ml of obsolute methanol, stirred for 1.5 hour and filtered, and the resulting crystals were dried over phosphorus pentoxide in a desiccator to give 34.3 g of white crystals of sodium salt of a cysteamine-S-phosphoric acid ester.

Yield: 95.7%.

Next, 34.3 g (0.192 mol) of the obtained sodium salt of a cysteamine-S-phosphoric acid ester was reacted with 680 ml of glacial acetic acid at 25° C. for one hour, and the precipitated crystals were filtered and washed with glacial acetic acid and petroleum ether.

The obtained cysteamine-S-phosphoric acid was dissolved in 340 ml of 10% acetic acid, and to the solution was added 1,025 ml of ethanol for crystallization and filtered. This operation was repeated twice and the resulting crystals were dried over phosphorus pentoxide in a dessicator to give 20.0 g of cysteamine-S-phosphoric acid.

Yield: 66.2%; Melting point: 157.6° C.

Elementary analysis (calcd. for $C_2H_8N_1O_3P_1S_1$):

|  | C | H | N | S |
|---|---|---|---|---|
| Calculated (%): | 15.29 | 5.13 | 8.91 | 20.40 |
| Found (%): | 15.52 | 5.72 | 8.88 | 20.35. |

What is claimed is:

1. A process for preparing a cysteamine-S-substituted compound of the formula:

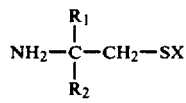

(wherein $R_1$ and $R_2$ may be same or different and each represents hydrogen or a lower alkyl group, X is $-SO_3H$, $-PO_3H_2$ or $-PO_3HM$, and M is an alkali metal, ammonium or a ½ alkaline earth metal element), comprising reacting an ethyleneimine derivative represented by the following formula:

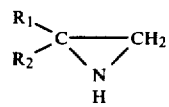

(wherein $R_1$ and $R_2$ are as defined above), with a thiosulfate or thiophosphate in the presence of a cation exchanger of the H+ form.

2. A process for preparing a cysteamine-S-substituted compound of the formula

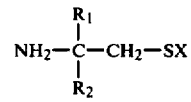

(wherein $R_1$ and $R_2$ may be same or different and each represents hydrogen or a lower alkyl group, X is $-SO_3H$, $-PO_3H_2$ or $-PO_3HM$, and M is an alkali metal, ammonium or a ½ alkaline earth metal element),
comprising reacting in a non-reactive solvent at a temperature greater than 0° C., an ethyleneimine derivative of the formula:

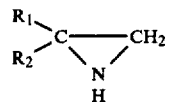

(wherein $R_1$ and $R_2$ are as defined above), with a thiosulfate or thiophosphate in the presence of a cation exchanger of the H+ form, and
recovering said cysteamine-S-substituted compound in pure form in a high yield by separating the cation exchanger in the reaction solution, concentrating the solution and then crystallizing the product.

* * * * *